United States Patent [19]

Sakai et al.

[11] Patent Number: 4,942,877
[45] Date of Patent: Jul. 24, 1990

[54] DEVICE FOR MEASURING OXYGEN SATURATION DEGREE IN ARTERIAL BLOOD

[75] Inventors: Takao Sakai, Habikino; Kenji Hamaguri, Osaka, both of Japan

[73] Assignee: Minolta Camera Kabushiki Kaisha, Osaka, Japan

[21] Appl. No.: 94,439

[22] Filed: Sep. 4, 1987

[30] Foreign Application Priority Data

Sep. 5, 1986 [JP] Japan .................. 61-209224

[51] Int. Cl.⁵ .............................. A61B 5/00
[52] U.S. Cl. .................... 128/633; 73/866.5; 356/41
[58] Field of Search ............... 128/633, 639; 364/550, 364/571; 356/41, 432; 73/866.5

[56] References Cited

U.S. PATENT DOCUMENTS

| | | | |
|---|---|---|---|
| 3,910,701 | 10/1975 | Henderson et al. | 356/39 |
| 4,303,984 | 12/1981 | Houvig | 364/571 |
| 4,418,392 | 11/1983 | Hata | 364/571 |
| 4,621,643 | 11/1986 | New, Jr. et al. | 128/633 |
| 4,636,934 | 1/1987 | Schwendemann | 364/550 X |
| 4,684,245 | 8/1987 | Goldring | 356/41 |

OTHER PUBLICATIONS

Continuous, Non-Invasive Measurements of Arterial Blood Oxygen Levels, Edwin B. Merrick et al., pp. 2-10, Hewlet-Packard Journal.

*Primary Examiner*—William E. Wayner
*Attorney, Agent, or Firm*—Price, Gess & Ubell

[57] ABSTRACT

An improved oximeter device for the calculation of oxygen saturation in arterial blood is provided. A pair of LED's are positioned to transmit red and infrared light through tissue containing the blood. A photo electric converter is provided to receive the transmitted light and convert it into a electrical signals. The probe can store data directed to various characteristics of the LED's, such as the primary wavelength and a secondary wavelength of the LED and an indication of the amount of crosstalk that can occur in the signals. The correction of any errors resulting from crosstalk plus the calculation of oxygen saturation depending on the various characteristics of the LED's can be effectuated.

28 Claims, 9 Drawing Sheets

| Intensity of main wavelength light of RLED |
| --- |
| Intensity of light of IRLED |
| wavelength of main wavelength light of RLED |
| half power width of main wavelength light of RLED |
| wavelength of sub-wavelength light of RLED |
| ratio of luminance of sub to main of RLED |
| wavelength of IRLED |
| half power width of IRLED |
| crosstalk amount from R-ch. to IR-ch. |
| crosstalk amount from IR-ch. to R-ch. |
| sum check data |

DEVICE FOR MEASURING OXYGEN SATURATION DEGREE IN ARTERIAL BLOOD

BACKGROUND OF THE INVENTION

1. FIELD OF THE INVENTION

The present invention relates to an oximeter device for measuring the oxygen saturation degree in arterial blood.

2. DESCRIPTION OF THE PRIOR ART

There has been proposed a probe calibration device of an oximeter device titled "CALIBRATED OPTICAL OXIMETER PROBE" (referred to as First Prior Example hereinafter) in the U.S. Pat. No. 4,621,643. The first prior example is characterized in that the probe device which is used together with the optical oximeter body for obtaining data of blood of a patient comprises;

light emitting means for emitting light of a known narrow wavelength range, a photosensor for detecting the intensity of the light passed through a patient to be measured, a coding means for applying the data signal of the known narrow wavelength to the optical oximeter body with respect to the probe and a connection device for attachably and removably attaching the coding means, the photosensor and the light emitting means to the oximeter body, whereby the oximeter body receives the data signal at the coding means so as to determine the frequency of light emitted by the light emitting means, and subsequently calculate the oxygen saturation based on the determined frequency.

There has been proposed a general organism data measuring device (referred to as Second Prior Example hereinafter) in the U.S. Pat. No. 4,418,392. The above mentioned organism data measuring device measures the data of the organism and comprises;

a transducer for measuring an organism data to be required and for converting the organism data into a corresponding electrical data, a memory means for storing a calibration data calculated in accordance with the reference characteristic of said transducer, a calibration means for calibrating the converted organism data based on the calibration data, a reading means for reading out the calibration data stored in the memory means, and a calibration control means for controlling the reading means to read out the calibration data and selecting a corresponding part of the calibration data to the organism data measured by the transducer, and for controlling the calibration means to calibrate the converted organism data in accordance with the selected part of the calibrated data.

In the above mentioned first prior example, the light of a predetermined wavelength radiated from the light emitting means is applied to the photosensor through the examined organism and the output of the photosensor is processed by a predetermined calculation so as to calculate the oxygen saturation degree $SaO_2$ in the arterial blood of the organism. But, for example, in case the light emitting means emit not only the light of a narrow wavelength range but also the light of a comparatively wide wavelength range or emit a light of another wavelength than the main wavelength (referred to as the light of a sub-wavelength), there occurs an error in the calculation value of the oxygen saturation degree $SaO_2$. Moreover, in case two light emitting means, for example, are used in order to calculate the oxygen saturation degree $SaO_2$ and the light emitting spectrums of the two emitting devices are overlapped with each other, or in case each data of the light emitted by the above mentioned two emitting means is mixed in the process of the calculation of the oxygen saturation degree $SaO_2$ and can not be obtained separately at the output of the processing circuit of the above mentioned calculation so that crosstalk exists, there has been a problem that there occurs an error in the calculation value of the oxygen saturation degree $SaO_2$.

Furthermore, the latter second prior example comprises a calibration means for performing the calibration process of the calculation data at the time of calculating the data of the organism, but the concrete means or ways of calculating the oxygen saturation degree are not disclosed.

SUMMARY OF THE INVENTION

An essential object of the present invention is to provide an oximeter device which is able to measure the oxygen saturation degree in the arterial blood of an organism to be examined correctly even though there is dispersion of the spectrums of the light emitting devices or there is a crosstalk as mentioned above.

The oximeter device according to the present invention comprises;

a probe device comprising light emitting means, light receiving means and memory means for storing data necessary for the calculation of the oxygen saturation degree in the arterial blood of the examined organism caused by the light emitting means and the light receiving means, and calculation means for reading out the data signal of the memory means and executing the calculation of the oxygen saturation degree on the basis of the read-out data signal and the output of the light receiving means when the probe device is connected to the oximeter device.

By the arrangement as mentioned above, the data necessary for the calculation of the oxygen saturation degree in the arterial blood of the examined organism caused by the light emitting means and the light receiving means are stored in the memory means and the data stored in the memory means are read out by the calculation means and then the calculation of the oxygen saturation degree is executed on the basis of the read-out data and the output of the light receiving means so as to obtain the oxygen saturation degree.

DETAILED DESCRIPTION OF THE PREFERRED EMBODIMENT

Figure 1:
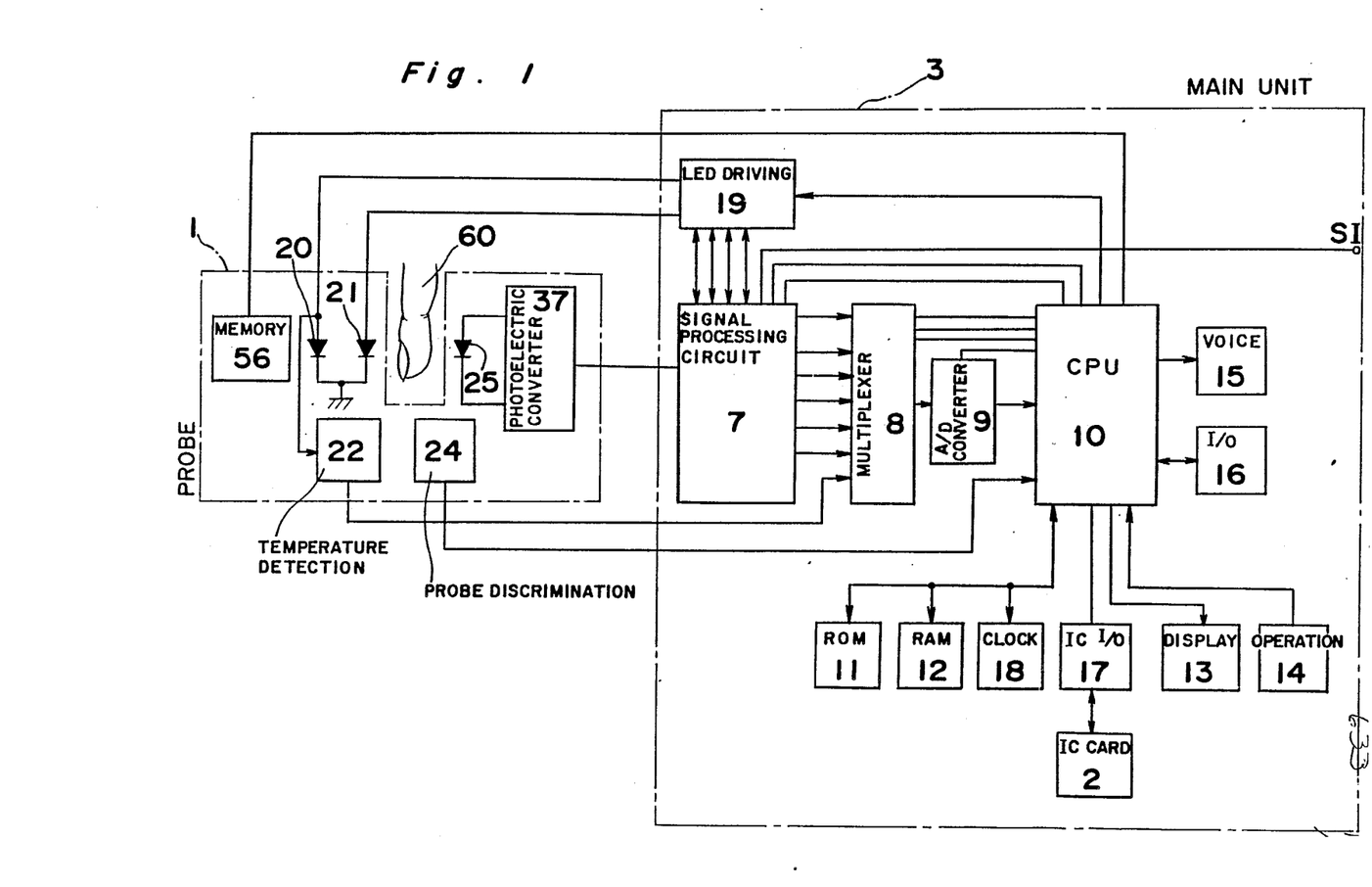
FIG. 1 is a block diagram showing an embodiment of an oximeter device according to the present invention.

In FIG. 1, the oximeter device comprises a probe 1 and a main unit 3. The probe 1 is detachably connected to the main unit 3. In the probe 1, there is provided a pair of a red light emitting diode 20 and an infrared ray emitting diode 21 disposed to project a red light and an infrared ray toward an object organism 60 such as a finger to be measured.

Figure 3:
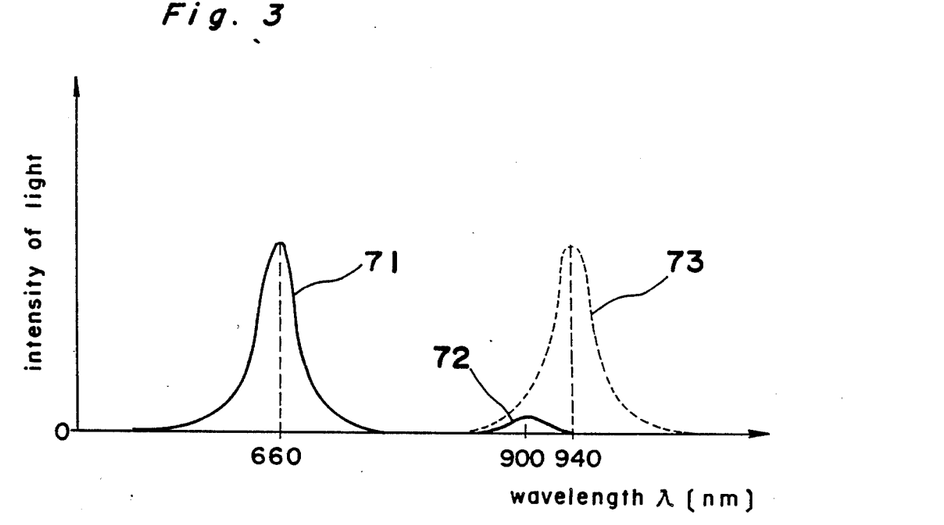
FIG. 3 is a graph diagram showing light emitting spectrum characteristics of a red light emitting diode and an infrared ray emitting diode of the oximeter device in FIG. 1.

The red light emitting diode (referred to as RLED hereinafter) 20 emits red light 71 (see FIG. 3) of the main wavelength such as nearly 660 nm and emitting infrared ray 72 of the sub-wavelength such as 900 nm of which the light intensity is lower than that of the main wavelength light as shown in FIG. 3. The infrared light emitting diode (referred to as IRLED hereinafter) 21 emits an infrared ray 73 of the wavelength of nearly 940 nm. A temperature detecting unit 22 is provided near the RLED 20 and IRLED 21 for generating a signal representing the temperature of RLED 20 or IRLED 21. A probe discrimination generator 24 generates the signal for indicating which of a spot measuring probe or a continuous measuring probe is used. A light receiving element 25 made of a photodiode is disposed at a position opposing to said RLED 20 and IRLED 21 so as to receive the light which is radiated from RLED 20 and IRLED 21 and passed through the organism 60, thereby generating a signal corresponding to the intensity of light passed through the organism 60. Moreover, there are provided a photoelectric converter 37 for converting the output of the light receiving element 25 into a signal of a predetermined level and a non-volatile memory circuit 56 which is connected to a central processing unit (referred to as CPU) 10 in the main unit 3 through a data bus and stores the data of the luminous spectrums of RLED 20 and IRLED 21 and the data of crosstalk amount and sum check data. In the above mentioned embodiment, though the non-volatile memory circuit 56 is connected to CPU 10 via the data bus, both of the devices 10 and 56 may be connected via a single line so as to transfer the data serially.

Figure 4:
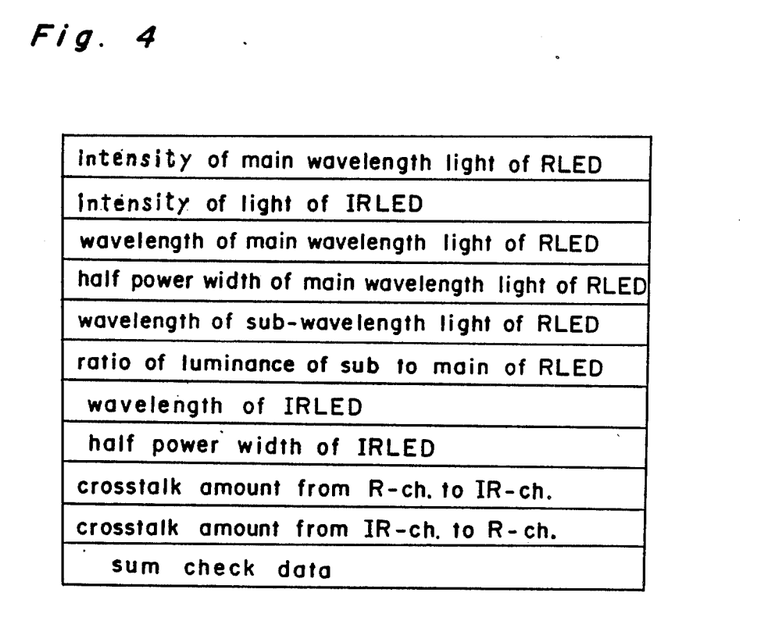
FIG. 4 is a diagram showing the data stored in a memory circuit in a probe of the oximeter device in FIG. 1, FIGS. 5a–5h are a timing chart showing a wave-form of each portion of the signal processing circuit in FIG. 2.

Moreover, the memory circuit 56 may be made of an EEPROM or EPROM in which the data can be electrically written and erased and may be made by a digital switch. As shown in FIG. 4, the memory circuit 56 stores eleven items with respect to the properties of the light or ray of the RLED 20 and IRLED 21 as follows;

(1) the intensity of the main wavelength light of RLED 20 when a predetermined driving current is supplied, (2) the intensity of the main wavelength light of IRLED 21 when a predetermined driving current is supplied, (3) the wavelength of the main wavelength light of RLED 20, (4) the half width of the main wavelength light of RLED 20, (5) the wavelength of the sub-wavelength light of RLED 20, (6) the ratio of the intensity of light of the sub-wavelength light to that of the main wavelength light of RLED 20, (7) the wavelength of the light of IRLED 21, (8) the half width of the light of IRLED 21, (9) the crosstalk amount caused in case of mixing the light signal of RLED 20 into the processing circuit of the light of IRLED 21 (referred to as crosstalk amount from R channel to IR channel hereinafter) to be described later, (10) the crosstalk amount caused in case of mixing the light signal of IRLED 21 into the processing circuit of the light of RLED 20 (referred to as crosstalk amount from IR channel to R channel hereinafter) to be described later, and (11) the sum check data.

The sum check data is so determined that the sum of the data (1) to (11) amounts to a predetermined value. The sum check data is used to detect whether each of the data (1) to (10) is correctly stored or not in the memory circuit 56.

There are provided in the main unit 3 a signal processing circuit 7 for processing the output of the light receiving element 25 in the probe 1 to be described later. A multiplexer 8 selects the output of the signal processing circuit 7, an analogue to digital converter 9 (referred to as A/D converter hereinafter) for converting the analogue output signal of the multiplexer 8 into a digital signal. CPU 10 calculates the oxygen saturation degree $SaO_2$ in arterial blood and the pulse rate of the organism 60 and controls a display unit 13 and an operating unit 14, a read only memory (referred to as ROM hereinafter) 11, and a random access memory (referred to as RAM hereinafter) 12. The display unit 13 displays the calculated oxygen saturation degree $SaO_2$ in the arterial blood and the pulse rate. The operation unit 14 selects an alarm level and a measuring mode/display mode of the oximeter device. A voice generator 15 generates an alarm sound and the sound of the pulse of the organism. An input-and-output interface 16 sends and receives the data to and from a printer and an external personal computer and generates the wave-form of the pulse. An IC card input and output unit 17 sends and receives the data of the calculation value to and from the IC card 2. 18 denotes a clock portion. A light emitting diode (referred to as LED) driving portion 19 supplies power to RLED 20 and IRLED 21 for turning them on.

The principle of calculating the oxygen saturation degree $SaO_2$ in the arterial blood according to the present embodiment will be explained. When the lights of wavelength $\lambda_1$ and $\lambda_2$ are radiated to the organism 60, the luminance intensities $I_1$ and $I_2$ of the lights of the wavelengths $\lambda_1$ and $\lambda_2$ having passed through the organism 60 may be represented as follows;

$$I_1 = I_{o1} \times Tt_1 \times \exp\{-g_1[(E_1O-E_1H) SaO_2/100 + E_1H] \times (d+\Delta d)\} \quad (1)$$

$$I_2 = I_{o2} \times Tt_2 \times \exp\{-g_2[(E_2O-E_2H) \times SaO_2/100 + E_2H] \times (d+\Delta d)\} \quad (2),$$

wherein $I_{o1}$: the intensity of the incident light of wavelength $\lambda_1$, $I_{O2}$: the intensity of the incident light of wavelength $\lambda_2$, $E_1O$: the absorption coefficient of oxyhemoglobin at the wavelength $\lambda_1$ of the light, $E_2O$: the absorption coefficient of oxyhemoglobin at the wavelength $\lambda_2$ of the light, $E_1H$: the absorption coefficient of hemoglobin at the wavelength $\lambda_1$ of the light, $E_2H$: the absorption coefficient of hemoglobin at the wavelength $\lambda_2$ of the light, $Tt_1$: the transmittance of the tissue other than the arterial blood at the wavelength $\lambda_1$ of the light, $Tt_2$: the transmittance of the tissue other than the arterial blood at the wavelength $\lambda_2$ of the light, d: the averaged thickness of the arterial blood layer, $\Delta d$: the variable component of the thickness of the arterial blood layer, $SaO_2$: the oxygen saturation degree in the arterial blood, $g_1, g_2$: the coefficient of the gain.

Assuming that the DC components of the luminances $I_1$ and $I_2$ of the lights of each wavelength after passing through the organism 60 are represented by $I_1DC$ and $I_2DC$ respectively and the values $\log(I_1DC/I_1)$ and $\log(I_2DC/I_2)$ are represented by $U_1$ and $U_2$ respectively, the values $U_1$ and $U_2$ may be approximately represented as follows;

$$U_1 = g_1[(E_1O - E_1H)SaO_2/100 + E_1H]\Delta d \quad (3)$$

$$U_2 = g_2[(E_2O - E_2H)SaO_2/100 + E_2H]\Delta d \quad (4)$$

Moreover, assuming that the values $U_1$ and $U_2$ may be obtained as the variable components of the values $\log I_1$ and $\log I_2$ and that the variable components of the intensities of lights $I_1$ and $I_2$ are $\Delta I_1$ and $\Delta I_2$, the values $U_1$ and $U_2$ may be obtained as the values $\Delta I_1/I_1DC$, $\Delta I_2/I_2DC$ respectively so as to obtain the expressions (3) and (4). Next, from the expressions (3) and (4), the value of the oxygen saturation degree $SaO_2$ in the arterial blood may be obtained as follows;

$$SaO_2 = \{K_1(U_1/U_2)^2 + K_2\}/\{K_3(U_1/U_2)^2 + K_4\} \times 100 \quad (5)$$

wherein the numerals $K_1$, $K_2$, $K_3$ and $K_4$ represent respectively constant values determined by the wavelengths $\lambda_1$ and $\lambda_2$. In the present embodiment, the wavelengths of approximately 660 nm and 940 nm are adopted as the wavelengths $\lambda_1$ and $\lambda_2$.

The arrangement of the signal processing circuit 7 in the device body 3 according to the present invention is explained with reference to FIG. 2.

Figure 5:
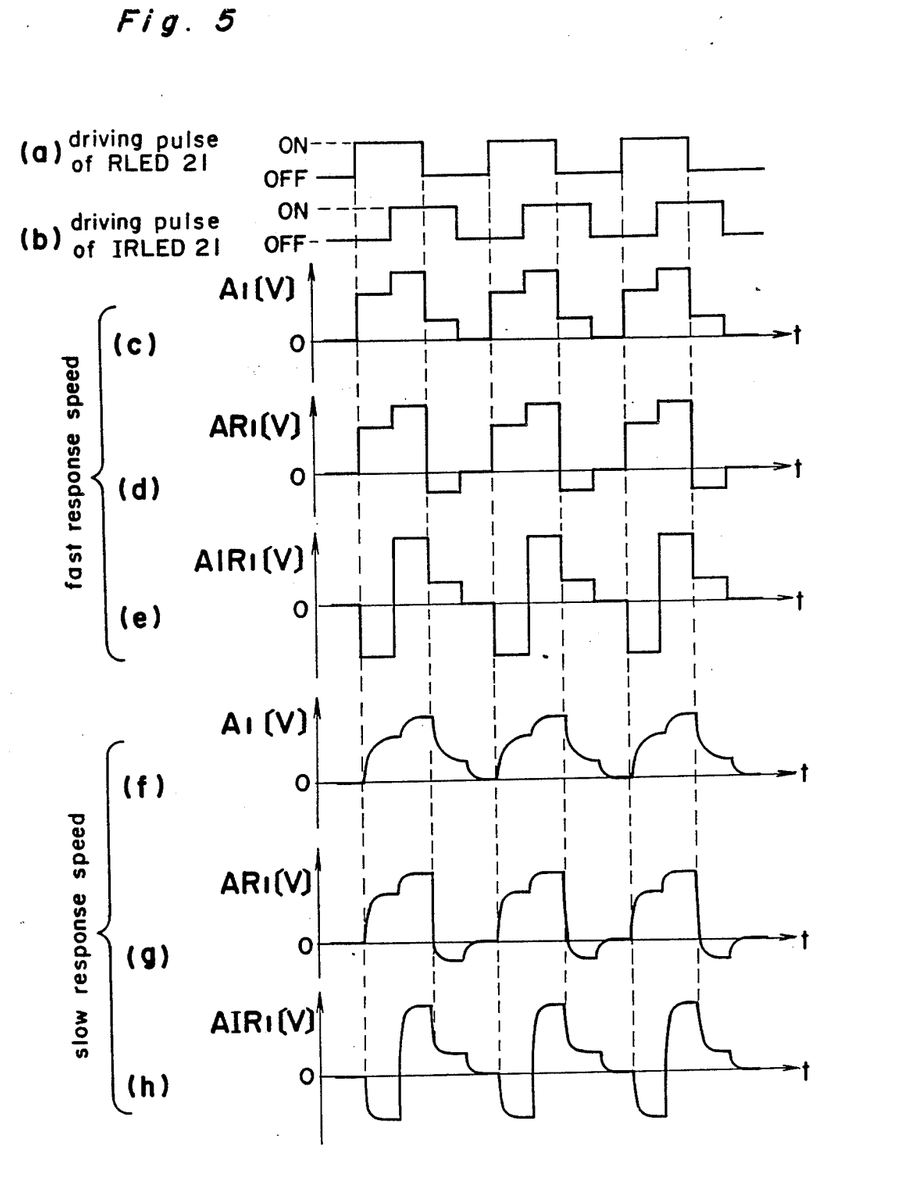

In the present embodiment, as described above, as the light sources there are mainly adopted RLED 20 emitting the red light of the wavelength nearly 660 nm and IRLED 21 emitting the infrared ray of the wavelength nearly 940 nm. Each of RLED 20 and IRLED 21 is respectively driven by the LED driving unit 19 which is controlled by the timing pulse generated by an oscillator included in CPU 10. The LED driving unit 19 generates two series of the driving periodic pulses having the same cycle, the phase difference of 90° and the duty ratio 50%. These pulses are fed to RLED 20 and IRLED 21 so as to turn RLED 20 and IRLED 21 on respectively as shown in FIGS. 5(a) and 5(b). The light emitted from RLED 20 and IRLED 21 passes through the organism 60 and are declined and then received by the light receiving element 25, which generates electric current corresponding to the intensity of the incident light and the generated current is converted into voltage through a photoelectric converter 37 and fed to the terminal $a_1$ of the switch $S_1$.

In case the device body 3 is set in the measuring mode, the switch $S_1$ is connected to the terminal $a_1$ so that the output of the photoelectric converter 37 is amplified through an amplifier 38 and in turn inputted to a R-synchronous rectifier 39 and an IR-synchronous rectifier 40. The R-synchronous rectifier 39 is synchronized with one of the two series of the driving periodic pulses, pulse (a) in FIG. 5 generated from the LED driving unit 19 and rectify the signal of red light inputted from the converter 37. In other words, the R-synchronous rectifier 39 amplifies the input signal by a gain of 1 while RLED 20 emits the light and amplifies the input signal by a gain of $-1$ while RLED 20 does not emit the light. Similarly, the IR-synchronous rectifier 40 is synchronized with another series of the driving periodic pulses (b) and amplifies the input signal by a gain of 1 while IRLED 21 emits the light and amplifies the input signal by a gain of $-1$ while IRLED 21 does not emit the light. The time average value of the output of the synchronous rectifiers 40 corresponds to the intensity of the light of only IRLED 21 passed through the organism 60. Therefore, the outputs of a R low-pass filter 41 and an IR low-pass filter 42 corresponds respectively to the intensity of the light of wavelengths around 660 nm and 940 nm having passed through the organism 60. Thus, when a signal of the light of the light receiving element 25 is separated into the signal representing only the light of wavelengths 660 nm and another signal representing the light of 940 nm, the influence of the external disturbance light can be removed by properly selecting the driving frequencies of RLED 20 and IRLED 21.

Figure 2:
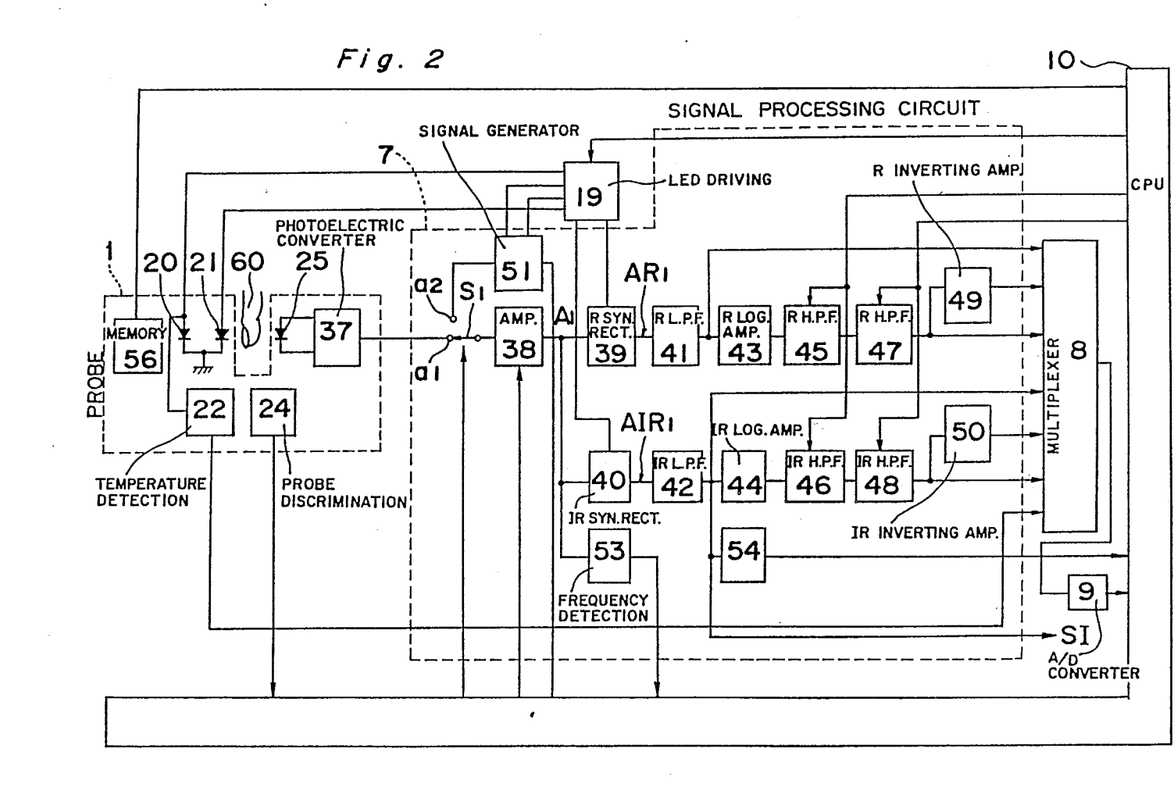
FIG. 2 is a block diagram showing a signal processing circuit of the oximeter device in FIG. 1.

In FIG. 2, a frequency detecting unit 53 detects the frequency of a commercial power source now in use and CPU 10 sets the driving frequency of RLED 20 and IRLED 21 to nearly (integer times of 60+30)Hz (when the commercial power source frequency is 60 Hz), or nearly (integer times of 50+25)Hz (when the commercial power source frequency is 50 Hz).

Furthermore, the outputs of the R low-pass filter 41 and the IR low-pass filter 42 are converted from analogue form to digital form (referred to as A/D hereinafter) by the A/D converter 9 via the multiplexer 8 and in turn inputted to CPU 10. CPU 10 calculates the ratio of the output of the R low-pass filter 41 to the output of the IR low-pass filter 42 and controls the LED driving unit 19 so that the ratio becomes within a predetermined range, adjusting the intensity of the light of RLED 20 and the intensity of the light of IRLED 21. By these operations, the S/N ratio of the output of the R low-pass filter 41 becomes nearly equal to the S/N ratio of the output of the IR low-pass filter 42 so as to keep a desired condition for processing the signal.

In FIG. 2, CPU 10 controls the gain of the amplifier 38 so that the outputs of the R low-pass filter 41 and the IR low-pass filter 42 are settled within a predetermined range. The output terminal of the IR low-pass filter 42 is connected to the signal line SI for the external output of the device body 3. In addition, the outputs of the R low-pass filter 41 and the IR low-pass filter 42 are respectively connected to a R logarithmic amplifier 43 and an IR logarithmic amplifier 44 and are inputted in the multiplexer 8 respectively via a R high-pass filter 45 and a R high-pass filter 47 and via an IR high-pass filter 46 and an IR high-pass filter 48. Moreover, the outputs of the R high-pass filter 47 and the IR high-pass filter 48 are inputted in the multiplexer 8 via a R inverting amplifier 49 and an IR inverting amplifier 50 respectively. In case the output of the R high-pass filter 47 or the IR high-pass filter 48 is positive, these outputs are converted from an analog form to a digital form by the A/D converter 9 via the multiplexer 8, but in case these outputs are negative, the outputs of the inverting amplifiers 49 and 50 are converted from an analog form to a digital form and applied to CPU 10. In addition, the outputs of the R low-pass filter 41 and the IR low-pass filter 42, the outputs of the R high-pass filter 47 or the R inverting amplifier 49, the outputs of the IR high-pass filter 48 or the IR inverting amplifier 50 are respectively converted from an analog form to a digital form in a predetermined sampling cycle by the A/D converter 9 and transmitted to CPU 10.

Referring to FIG. 3 showing the light emitting spectrum of RLED 20 and IRLED 21 in the probe 1, since RLED 20 emits not only the main wavelength light 71 but also the sub-wavelength light 72 and there inevitably exist dispersions of the wavelength, intensity of emitting light and half width in the spectrum characteristics of RLED 20 and IRLED 21, if the oxygen saturation degree $SaO_2$ in the arterial blood is calculated by using the expression (5), there occurs an unnegligible error. This is because when the light of RLED 20 and IRLED 21 is radiated to the organism 60, the intensities $I_1$ and $I_2$ of the respective light passing through the organism 60 are strictly represented as follows.

$$I_1 = \int Io_1(\lambda) \times T_t(\lambda) \times \exp\{-g_1(EO(\lambda)-EH(\lambda)) \times SaO_2/100 + EH(\lambda) \times (d+\Delta d)\}d\lambda \quad (6)$$

$$I_2 = \int Io_2(\lambda) \times T_t(\lambda) \times \exp\{-g_2(EO(\lambda)-EH(\lambda)) \times SaO_2/100 + EH(\lambda) \times (d+\Delta d)\}d\lambda \quad (7)$$

wherein $Io_1(\lambda)$: the light emitting spectrum character of RLED 20

$Io_2(\lambda)$: the light emitting spectrum character of IRLED 21

$T_t(\lambda)$: the spectral transmittance of tissue except arterial blood $EO(\lambda)$: the spectral absorption coefficient of oxyhemoglobin $EH(\lambda)$: the spectral absorption coefficient of hemoglobin d, $\Delta d$, $SaO_2$, $g_1$ and $g_2$ are same as those in the expression (1).

The oxygen saturation degree $SaO_2$ in the arterial blood can be obtained by the calculation of the expression (5) based on the measured value inputted in CPU 10 when there is no error at the time of separating the light signal from RLED 20 and the light signal from IRLED 21 in the R synchronous rectifier 39 and the IR synchronous rectifier 40. However, in case the response speeds of the light receiving element 25, the photoelectric converter 37, the amplifier 38, the R synchronous rectifier 39 and the IR synchronous rectifier 40 are slow compared with the driving frequencies of RLED 20 and IRLED 21, and when the sub-wavelength 900 nm of the light of RLED 20 is near the wavelength 940 nm of IRLED 21 as shown in FIG. 3, the output AR1 of the R synchronous rectifier 39 contains the signal representing the light from IRLED 21 as a crosstalk and similarly the output AIR1 of the IR synchronous rectifier 40 contains the signal representing the light from RLED 20 as a crosstalk.

For example, in case the response speeds of the light receiving element 25, the photoelectric converter 37, the amplifier 38, the R synchronous rectifier 39 and the IR synchronous rectifier 40 are fast compared with the driving frequencies of RLED 20 and IRLED 21, the output A1 of the amplifier 38, the output AR1 of the R synchronous rectifier 39 and the output AIR1 of the IR synchronous rectifier 40 are changed in respective levels immediately in response to the driving signal of each of RLED 20 and IRLED 21 so that the crosstalk is not produced as shown in FIGS. 5(c), 5(d) and 5(e). However, in case the response speeds of the light receiving element 25, the photoelectric converter 37, the amplifier 38, the R synchronous rectifier 39 and the IR synchronous rectifier 40 are slow compared with the driving frequencies of RLED 20 and IRLED 21, the output A1 of the amplifier 38, the output AR1 of the R synchronous rectifier 39 and the output AIR1 of the IR synchronous rectifier 40 do not immediately respond to the driving signal of each of the RLED 20 and IRLED 21 but each level thereof is transitionally changed as shown in FIGS. 5(f), 5(g) and 5(h) so as to produce the crosstalk.

Among the above mentioned crosstalks, the crosstalk caused by only the probe 1 to be stored in the memory 56 is obtained by subtracting the crosstalk caused by the main unit 3 from the crosstalks caused by the probe 1 and the main unit 3. In order to obtain the crosstalk in the probe 1 only RLED 20 is continuously turned on, while IRLED 21 is turned off. At this time, in case of absence of the crosstalk, the R low-pass filter 41 generates a predetermined output value but the IR low-pass filter 42 generates no output at all. However, in case the crosstalk is present, the crosstalk from the R channel to the IR channel exists in the output of the IR low-pass filter 42. Therefore, the crosstalk from the R channel to the IR channel caused by the circuits including the probe 1 and the amplifier 38 to the low-pass filter 41 or 42 can be obtained by calculating the ratio of the output of the IR low-pass filter 42 to the output of the R low-pass filter 41. Similarly, the crosstalk from the IR channel to the R channel caused by the circuits including the probe 1 and the amplifier 38 to the low-pass filter 41 and 42 can be obtained by calculating the ratio of the output of the R low-pass filter 42 to the output of IR low-pass filter 41.

Moreover, upon switching the switch S1 from the terminal $a_1$ to the terminal $a_2$ and applying the revision signal of a predetermined wavelength from a crosstalk measuring revision signal generator 51 to the amplifier 38, the crosstalk amount from the R channel to the IR channel and the crosstalk amount from the IR channel to the R channel which are caused by the circuits of the main unit 3 including the amplifier 38 to the low-pass filter 41 or 42 can be obtained.

As described above, the crosstalk caused by the probe 1 can be obtained by subtracting the crosstalk caused by the circuits of the main unit 3 including the amplifier 38 to the low-pass filters 41 and 42 from the crosstalk caused by the circuits including the probe 1 and the amplifier 38 to the low-pass filter 41 and 42.

Next, the operation of the oximeter device shown in FIGS. 1 and 2 will be explained with reference to the flow charts shown in FIGS. 6 and 7.

In the step 1, when the power switch of the main unit 3 is turned on, the program goes to the step 2 and CPU 10 reads out the above mentioned eleven data items (shown in FIG. 4) stored in the memory circuit 56 in the probe 1 and stores them in RAM 12. In the next step 3-1, CPU 10 adds all the data read out in the step 2. It is judged in the step 3-2 whether or not the added value is equal to a predetermined value, whereby it is judged whether or not the probe 1 is connected to the main unit 3 correctly and whether or not the contents of the data stored in the memory circuit 56 in the probe 1 are destroyed, in other words, the data stored in the memory circuit 56 are correctly read out by CPU 10. In the step 3-2, in case the added value is not equal to the predetermined value, in other words, in case the data stored in the memory circuit 56 are not correctly read out, the program goes to the step 4 and CPU 10 displays the error on the display unit 13 in the oximeter main unit 3 and then in the step 5 the operation of the oximeter device is stopped. In the memory circuit 56 in the probe 1, the sum check data are stored in the memory circuit so that when all the data stored in the memory circuit 56 are added, the added value is equal to the predetermined value.

On the other hand, in case it is detected in the step 3-2 that the data stored in the memory circuit 56 are correctly read out, the program goes to the step 6 and a predetermined LED driving current of the LED driving unit 19 is selected respectively depending on the data signal of the intensity of the light of the main wavelength of RLED 20 and the intensity of the light of IRLED 21 among the data stored in RAM 12. In other words, in case the intensity of the light of LED is small, the LED driving current is made large and in case the intensity of the light of LED is large, the LED driving current is made small, thereby controlling RLED 20 and IRLED 21 so as to emit a predetermined light amount.

In the next step 7, the coefficients $K_1$ to $K_4$ in the calculation of the oxygen saturation degree $SaO_2$ in the arterial blood are obtained by the light emitting spectrums of RLED 20 and IRLED 21. According to the expressions (6) and (7) as described above, the intensities $I_1$ and $I_2$ of the light which has been radiated from RLED 20 and IRLED 21 to the organism 60 and pass through the organism 60 are affected by the light emitting spectrum character $Io_1(\lambda)$ of RLED 20 and the light emitting spectrum character $Io_2(\lambda)$ of IRLED 21. But since a large memory capacity is required in order to store the light emitting spectrum characters of RLED 20 and IRLED 21, in the present embodiment, the wavelength and the half width (shown as H.W. in Table 1) of the main wavelength light of RLED 20, the wavelength of the sub-wavelength light of RLED 20, the ratio of the light emitting intensity of the sub-wavelength light to that of the main wavelength light of RLED 20 and the wavelength and the half width (shown as H.W. in Table 1) of IRLED 21 are stored as the values representing the light emitting spectrum. In the step 7, depending on the stored values mentioned above, the coefficients $K_1$ to $K_4$ in the expression (5) of the calculation of the oxygen saturation degree $SaO_2$ in the arterial blood are selected from the table of the coefficients $K_1$ to $K_4$ of the expression of the oxygen saturation degree $SaO_2$ corresponding to the light emitting spectrum character of various kinds of LED stored previously in ROM 11. The table of the coefficients $K_1$ to $K_4$ of the expression of the oxygen saturation degree $SaO_2$ is stored in ROM 11 as shown in Table 1. For example, in case the wavelength of the main wavelength light of RLED 20 is 660 nm, the half width (H.W.) of the main wavelength light of RLED 20 is 15 nm, the wavelength of the sub-wavelength light of RLED 20 is 900 nm, and the ratio of the light emitting intensity of the sub-wavelength light to that of the main wavelength of RLED 20 is 3%, and the wavelength of IRLED 21 is 935 nm, the half width (H.W.) of IRLED 21 is 40 nm, the coefficients $K_1$ to $K_4$ in the expression of the oxygen saturation degree $SaO_2$ are respectively $e_1$, $e_2$, $e_3$ and $e_4$ according to the table shown in Table 1. Moreover, in the above mentioned values, in case only the half width (H.W.) of IRLED 21 is 50 nm and the other values of the spectrum characters are same as above, the coefficients $K_1$ to $K_4$ are respectively $f_1$, $f_2$, $f_3$ and $f_4$.

Moreover, the table of the coefficients $K_1$ to $K_4$ in the expression of the oxygen saturation degree $SaO_2$ corresponding to the light emitting spectrum characters of the various kinds of LED is made as follows.

According to the expressions (6) and (7), the intensities $I_1$ and $I_2$ of the light radiated from each of the LED and passing through the organism 60 are calculated. Next, the photoelectric pulse signal is simulated with changing the values of $\Delta d$ in the expressions (6) and (7) and the values of $\log(I_1DC/I_1)$ and $\log(I_2DC/I_2)$ are obtained to be represented $U_1$ and $U_2$ respectively. Next, the values $U_1$ and $U_2$ are obtained to the plurality of the oxygen saturation degrees $SaO_2$, resulting in that the most preferable coefficients $K_1$ to $K_4$ in the expression (5) of the oxygen saturation degree $SaO_2$ in the arterial blood are determined.

Figure 7:
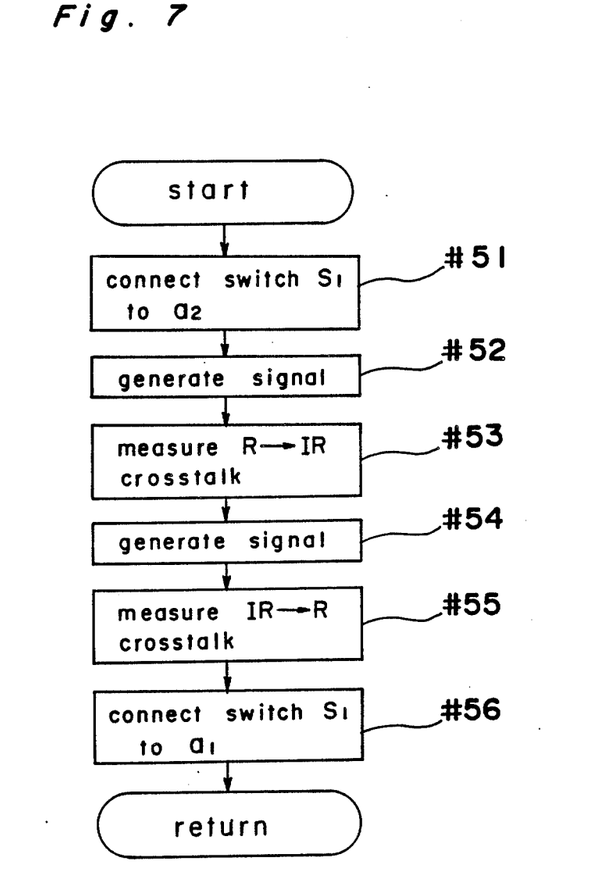
FIG. 7 is a flow chart showing the operation at the time of measuring the crosstalk in the oximeter body in FIG. 1.
Figure 8:
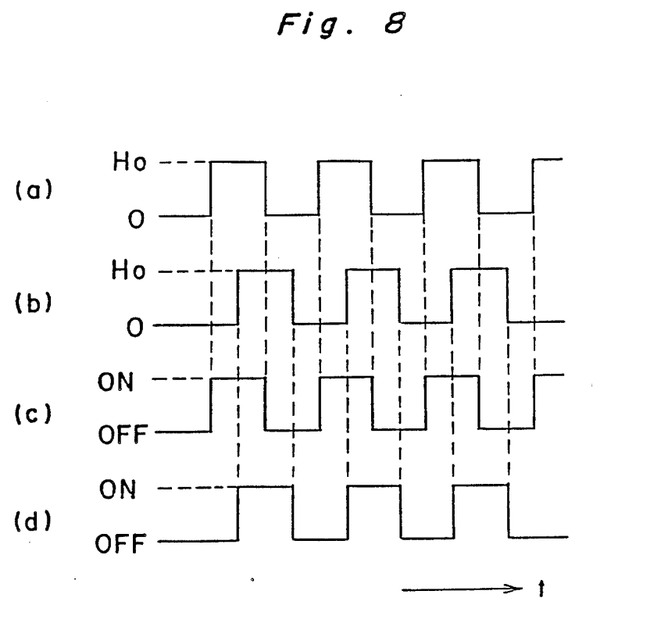
FIG. 8 is a timing chart showing input and output wave-forms of a revision signal generator 51 for measuring the crosstalk in the signal processing circuit in FIG. 2, and FIGS. 9 and 10 are flow charts showing modification of the operation shown in FIG. 6.

In the next step 8, the crosstalk amount in the main unit 3 is measured according to the operation shown in the flow chart in FIG. 7. In the step 51, after CPU 10 connects the switch $S_1$ to the contact point $a_2$, the crosstalk measuring revision signal generator 51 is synchronized with the driving signal (see FIG. 8(c)) of RLED 20 generated from the LED driving unit 19 and as shown in FIG. 8(a), a periodical pulse of a predetermined level H0 having the same cycle as the driving signal of RLED 20 is transmitted to the amplifier 38 via the point $a_2$ of the switch $S_1$. The output of the amplifier 38 is fed to the A/D converter 9 via the R synchronous rectifier 39, R low-pass filter 41 and the multiplexer 8 and the output of the amplifier 38 showing the intensity of the light of red light passed through the organism is converted from analog form to digital form and then transmitted to CPU 10, and at the same time, the output of the amplifier 38 is fed to the A/D converter 9 via the IR synchronous rectifier 40, IR low-pass filter 42 and the multiplexer 8 and the output of the amplifier 38 showing the intensity of the light of red light passed through the organism is converted from analog form to digital form and then transmitted to CPU 10.

When the periodical pulse shown in FIG. 8(a) is supplied to the amplifier 38 to generates its output, only RLED 20 is driven, and the crosstalk amount from the R channel to the IR channel can be obtained by calculating the ratio of the A/D converted value of the output of the R low-pass filter 41 (referred to as A/D converted value of the R channel hereinafter) to the A/D converted value of the output of the IR low-pass filter 42 (referred to as A/D converted value of the IR channel hereinafter) in the step 53 on the basis of the two A/D converted values transmitted to CPU 10.

In the next step 54, the crosstalk measuring revision signal generator 51 synchronizes with the driving signal shown in FIG. 8(d) for driving IRLED 21 generated from the LED driving unit 19 and transmits a series of periodical pulse of a predetermined level H0 having the same cycle as the driving signal as shown in FIG. 8(b) to the amplifier 38 via the point $a_2$ of the switch $S_1$. The output of the amplifier 38 is transmitted to CPU 10 via the R synchronous rectifier 39, the R low-pass filter 41, the multiplexer 8 and the A/D converter 9 and at the same time transmitted to CPU 10 via the IR synchronous rectifier 40, the IR low-pass filter 42, the multiplexer 8 and the A/D converter 9.

When the periodical pulse shown in FIG. 8(b) is transmitted to the amplifier 38, only IRLED 21 is periodically driven, therefore, the crosstalk amount from the IR channel to the R channel can be obtained by calculating the ratio of the A/D converted value of the IR channel to the A/D converted value of the R channel in the step 55 on the basis of the two A/D converted values transmitted to CPU 10. Subsequently, in the step 56, the switch $S_1$ is switched from the point $a_2$ to the point $a_1$ and the measurement of the crosstalk amount in the main unit 3 in the step 8 shown in FIG. 6 is completed.

In the next step 9, the crosstalk amount in the probe 1 stored in RAM 12 in the step 2 is added to the crosstalk amount in the main unit 3 calculated in the step 8 and the crosstalk amount of the whole measurement system of the oximeter device according to the present invention is obtained and stored in RAM 12 and used in the calculation of the oxygen saturation degree $SaO_2$ in the arterial blood.

The way of the calibration of the crosstalk amount in the calculation of the oxygen saturation degree $SaO_2$ in the arterial blood will be explained hereinafter. Assuming that the crosstalk amount from the R channel to the IR channel is $B_1$ and the crosstalk amount from the IR channel to the R channel is $B_2$, the output $P_1$ of the R high-pass filter 47 and the output $P_2$ of the IR high-pass filter 48 are represented as follows.

$$P_1 = U_1 + B_2 U_2 \quad (8)$$

$$P_2 = U_2 + B_1 U_1 \quad (9)$$

Therefore, the values $U_1$ and $U_2$ in the expression (5) can be obtained from the expression (8) and (9) as follows.

$$U_1 = (P_1 - B_2 P_2)/(1 - B_1 B_2) \quad (10)$$

$$U_2 = (P_2 - B_1 P_1)/(1 - B_1 B_2) \quad (11)$$

By the operation described above, the preparation for measuring the oxygen saturation degree $SaO_2$ in the arterial blood is completed, subsequently in the step 10 RLED 20 and IRLED 21 are driven by the LED driving unit 19 and the output $P_1$ of the R high-pass filter 47 and the output $P_2$ of the IR high-pass filter 48 are calculated, whereby the oxygen saturation degree $SaO_2$ in the arterial blood can be obtained by the calculation using the expressions (5), (10) and (11) on the basis of the A/D converted values of the above mentioned measured outputs $P_1$ and $P_2$. In the next step 11, by using a known method, the pulse rate per a minute is measured on the basis of the output of the photoelectric converter 37 and finally the obtained oxygen saturation degree $SaO_2$ and the pulse rate are displayed on the display unit 13.

Moreover, it is judged in the step 13 whether or not the measurement of the oxygen saturation degree in the arterial blood and the pulse rate is finished, and in case the measurement has not been completed, the program goes to the step 10 and the above mentioned process is repeated, while in case the measurement has been finished, the program goes to the step 14 and the operation of the oximeter device is stopped.

In the embodiment mentioned above, though the eleven data items of the properties of RLED and IRLED including the sum check data are stored in the memory circuit 56 in the probe 1, the table of the coefficients $K_1$ to $K_4$ used in the equation (5) for the calculation of the oxygen saturation degree $SaO_2$ in the arterial blood corresponding to RLED 20 and IRLED 21 in the probe 1 may be stored in the memory circuit 56 instead of storing the above mentioned eleven data items. Otherwise, the table of the coefficients $K_1$ to $K_4$ of the calculation of the reference oxygen saturation degree $SaO_2$ in the arterial blood may be preliminarily stored in ROM 11 in the main unit 3 and the calibration amount from the reference value may be stored in the memory circuit 56 in the probe 1.

In the embodiment mentioned above, although the coefficients $K_1$ to $K_4$ of the calculation of the oxygen saturation degree $SaO_2$ in the arterial blood corresponding to the light emitting spectrum characteristics of RLED 20 and IRLED 21 are stored in ROM 11, the calculation table of the reference oxygen saturation degree $SaO_2$ may be stored in ROM 11 and the calibration amount of the data of the calculation table may be stored in the memory circuit 56 in the probe 1.

In addition, CPU 10 reads out all or a part of the data stored in the memory circuit 56 in the probe 1 in a predetermined period and compares them with the data which is read out when the power source is turned on and which is stored in RAM 12, whereby it may be judged whether or not the probe 1 is exactly connected to the main unit.

Figure 6:
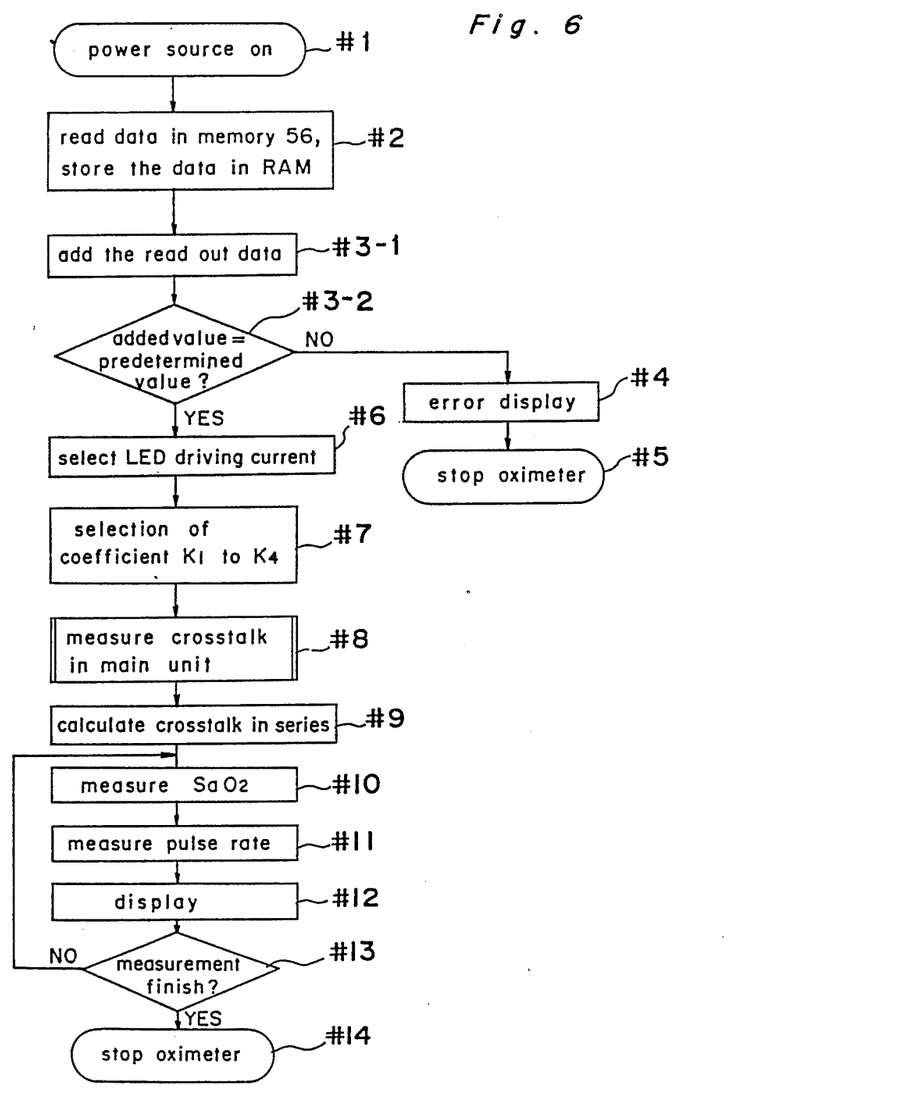
FIG. 6 is a flow chart showing the operation of the oximeter device in FIG. 1.
Figure 10:
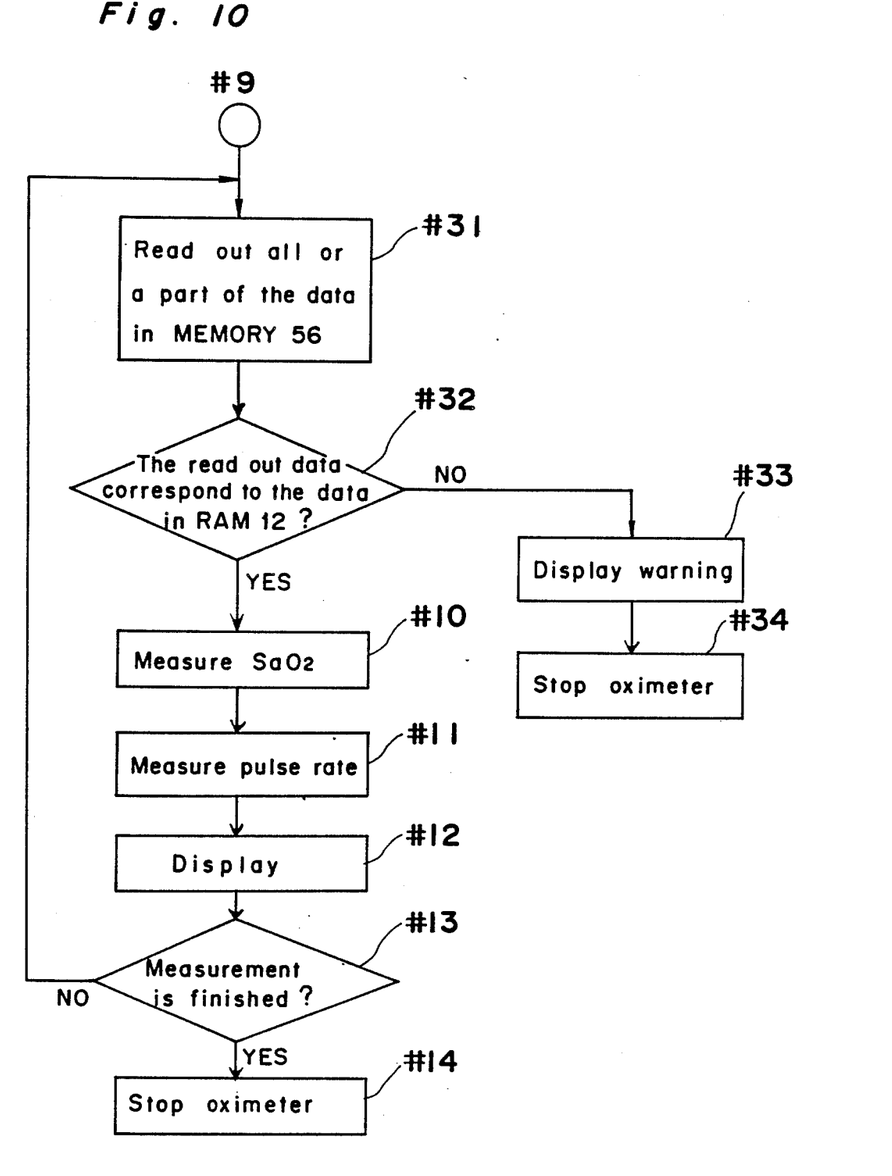

The operation of the modification mentioned above is shown in FIG. 10, which corresponds to the steps 10 to 14 in FIG. 6. Referring to FIG. 10, in the step 31, all or a part of the data stored in the memory circuit 56 in the probe 1 are read out, and it is judged in the step 32 whether or not the read out data correspond to the data which is read out when the power source is turned on and which is stored in RAM 12. In case of corresponding to the data, the program goes to the steps 10 (measure $SaO_2$), 11 (measure pulse rate), 12 (display) and in the next step 13 it is judged whether or not the measurement of the oxygen saturation degree and the pulse rate is finished and in case the measurement is not finished, the program goes back to the step 31. In the step 32 in case the read out data does not correspond to the data stored in RAM 12, the program goes to the step 33 and the warning that the data stored in the memory circuit 56 in the probe 1 are destroyed or the probe 1 is not exactly connected to the main unit 3, is displayed and in the next step 34 the operation of the oximeter device is stopped.

In case the memory circuit 56 in the probe 1 is a rewritable memory such as an EEPROM, the time of turning on RLED 20 and IRLED 21 in the probe 1 may be stored as follows. That is, the data of the time of turning on RLED 20 and IRLED 21 stored in the memory circuit 5i in the probe 1 may be re-written by CPU 10 in a predetermined period corresponding to the time when RLED 20 and IRLED 21 are turned on.

It is generally known that the intensity of light of LED decreases as the lighting time of LED. Therefore, the present intensity of light of each of RLED 20 and IRLED 21 may be presumed on the basis of the intensity of light of RLED 20 and IRLED 21 stored in the memory circuit 56 and the lighting time length, whereby the driving current of the LED driving unit 19 may be adjusted so as to maintain a desired intensity of light of RLED 20 and IRLE 21. It is also possible to indicate the life of the LED on the display unit 13.

Figure 9:
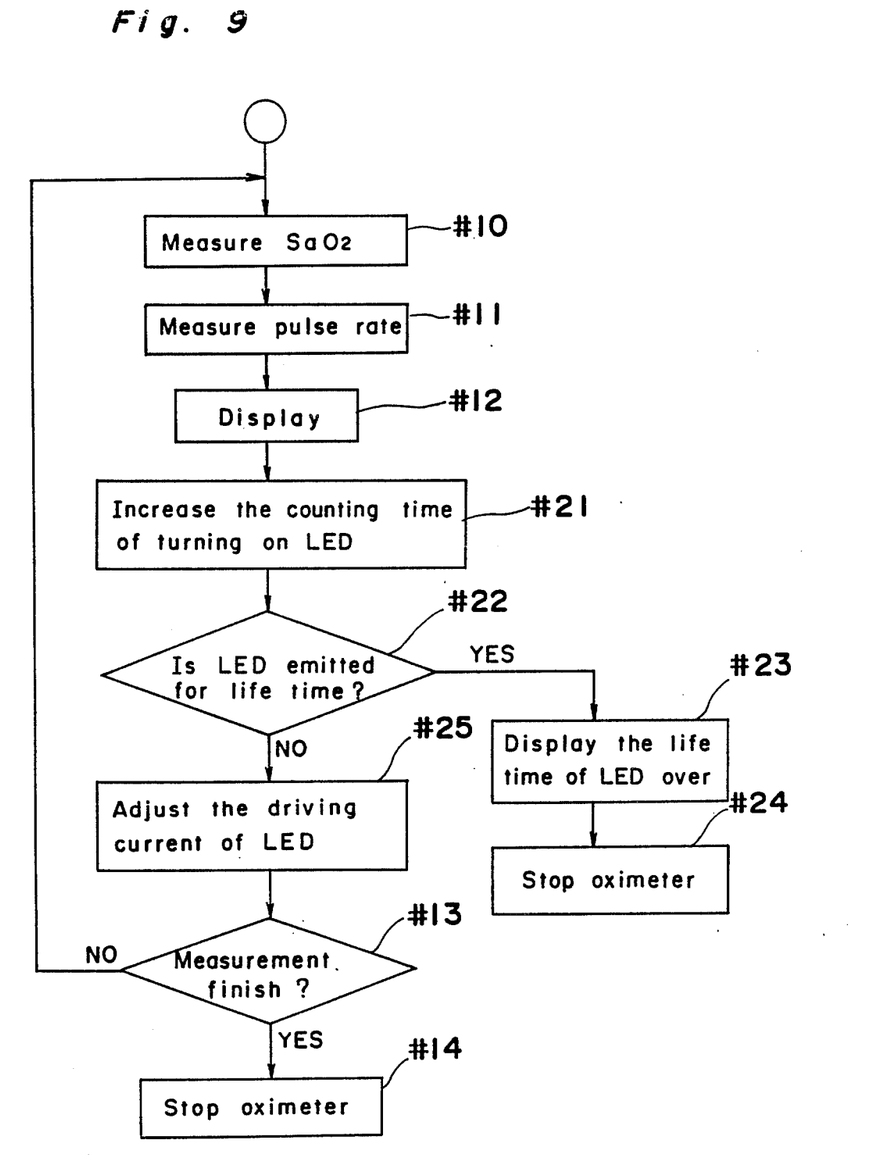

Referring to the method of storing the time of turning on the LED, the operation flow is shown in FIG. 9. The flow in FIG. 9 is a replacement of the portion of the steps 10 to 14 in FIG. 6. In the step 10 the oxygen saturation degree $SaO_2$ is measured, in the step 11 the pulse rate is measured and in the next step 12 each of the measured values is displayed. In the next step 21, the data of the counting time of turning on LED stored in the memory circuit 56 in the probe 1 are increased. It is judged in the step 22 whether or not the counting time of turning on LED reaches the life time of LED, and in case the counting time of turning on LED reaches the life time of LED, it is displayed on the display unit 13 in the step 23 that the life of LED is over and in the next step 24 the operation of the oximeter device is stopped. In case the counting time of turning on LED does not reach the life time of LED, the driving current of each of LED 20 and 21 is adjusted on the basis of the counting time of turning on LED it the step 25 and then the program goes to the step 13.

TABLE 1

| RLED MAIN W.L. | RLED MAIN H.W. | RLED SUB. W.L. | RLED SUB. INTEN. | IRLED W.L. | IRLED H.W. | $K_1$ | $K_2$ | $K_3$ | $K_4$ |
|---|---|---|---|---|---|---|---|---|---|
| 660 nm | 15 nm | 900 nm | 3% | 925 nm | 30 nm | $a_1$ | $a_2$ | $a_3$ | $a_4$ |
| 660 | 15 | 900 | 3 | 925 | 40 | $b_1$ | $b_2$ | $b_3$ | $b_4$ |
| 660 | 15 | 900 | 3 | 925 | 50 | $c_1$ | $c_2$ | $c_3$ | $c_4$ |
| 660 | 15 | 900 | 3 | 935 | 30 | $d_1$ | $d_2$ | $d_3$ | $d_4$ |
| 660 | 15 | 900 | 3 | 935 | 40 | $e_1$ | $e_2$ | $e_3$ | $e_4$ |
| 660 | 15 | 900 | 3 | 935 | 50 | $f_1$ | $f_2$ | $f_3$ | $f_4$ |
| ⋮ | ⋮ | ⋮ | ⋮ | ⋮ | ⋮ | ⋮ | ⋮ | ⋮ | ⋮ |
| 665 | 15 | 900 | 3 | 935 | 30 | $g_1$ | $g_2$ | $g_3$ | $g_4$ |
| 665 | 15 | 900 | 3 | 935 | 40 | $h_1$ | $h_2$ | $h_3$ | $h_4$ |
| 665 | 15 | 900 | 3 | 935 | 50 | $i_1$ | $i_2$ | $i_3$ | $i_4$ |

What is claimed is:

1. An oximeter device for measuring the saturation degree of oxygen in arterial blood, comprising:
   a probe having light emitting means for emitting light to an organism to be measured; light receiving means for receiving light from the organism and memory means for storing data necessary for a calculation of a saturation degree of oxygen in arterial blood of an examined organism caused by said light emitting means and said light receiving means, the memory means including a storage of data representative of crosstalk of light received by the light receiving means;
   a main unit having a calculation means which reads out the data stored in said memory means and calculates the saturation degree of oxygen on the basis of the read out data nd the output of said light receiving means, and
   means for connecting said probe to said main unit.

2. The oximeter device according to claim 1, further comprising means for computing the remaining operative life of the emitting means and a display unit for indicating the life of said light emitting means.

3. The oximeter device according to claim 1, wherein sum check data is stored in said memory means for judging whether or not the contents of the memory means have been destroyed and whether or not the probe is operatively connected to the main unit.

4. The oximeter device according to claim 2 further including means for counting the emitting time of said light emitting means and estimating the light emitting intensity corresponding to the time of turning on said light emitting means and adjusting a driving current for said light emitting means based on the intensity and the emitting time.

5. The oximeter device according to claim 4 wherein the light emitting means includes light emitting diodes.

6. An oximeter device for measuring the saturation degree of oxygen in arterial blood, comprising:
   a probe having light emitting means for emitting light to an organism to be measured, light receiving means for receiving light from the organism, and memory means for storing data necessary for a calculation of a saturation degree of oxygen in arterial blood of an examined organism caused by said light emitting means and said light receiving means;
   a main unit having a calculation means which reads out the data stored in said memory means and calculates the saturation degree of oxygen on the basis of the read out data and the output of said light receiving means, and
   means for detachably connecting said probe to said main unit, the memory means also storing a sum check data for enabling a judgment of whether or not the contents of the memory means are destroyed and whether or not the probe is exactly connected to the main unit.

7. An oximeter device for measuring the saturation degree of oxygen in arterial blood, comprising:
   a probe having light emitting means for emitting light to an organism to be measured, light receiving means for receiving light from the organism, and memory means for storing data necessary for a calculation of a saturation degree of oxygen in arterial blood of an examined organism caused by said light emitting means and said light receiving means, said memory means storing data representative of a predetermined value corresponding to actual stored data necessary for calculation;

a main unit having a calculation means which reads out the data stored in said memory means and calculates the saturation degree of oxygen on the basis of the read out data and the output of said light receiving means;

means for detachably connecting said probe to said main unit, and means in said main unit for reading out in a predetermined time period said stored data and comparing the stored data with the stored predetermined value data, whereby it is judged whether or not the probe is operatively connected to said main unit.

8. An oximeter device for measuring the saturation degree of oxygen in arterial blood, comprising:

a probe having light emitting means for emitting light to an organism to be measured, light receiving means for receiving light from the organism, memory means for storing data necessary for a calculation of a saturation degree of oxygen in arterial blood of an examined organism caused by said light emitting means and said light receiving means, said memory means including either an EEPROM or EPROM in which data an be rewritten, and means for counting the emitting time of said light emitting means and estimating the light emitting intensity corresponding to the time of turning on said light emitting means and adjusting a driving current for said light emitting means;

a main unit having a calculation means which reads out the data stored in said memory means and calculates the saturation degree of oxygen on the basis of the read out data and the output of said light receiving means; and means for connecting said probe to said main unit.

9. The oximeter device according to claim 8, wherein said memory means also stores on the crosstalk of said light receiving means.

10. The oximeter device according to claim 8, further comprising a display unit means for indicating the estimated remaining life of said light emitting means.

11. An improved oximeter device comprising:

a probe having a first light emitting diode means for emitting a predetermined first wavelength on light and a second light emitting diode means for emitting a predetermined second wavelength of light, light receiving means for receiving the emitted light and converting it into electrical signals for subsequent processing, and memory means for storing data characteristic of the probe to permit a calibration for the processing of the electrical signals to determine the degree of saturation of oxygen in the blood of an examined organism, the memory means further including the storage of data representative of crosstalk of light received by the light receiving means between the first and second wavelengths of light;

a main unit having a processor circuit for receiving the data stored in the memory means of the probe unit for calculating the saturation degree of oxygen on the basis of the stored data and the electrical signals of the light receiving means, and means for connecting the probe to the main unit.

12. The oximeter device according to claim 11, further comprising means for computing the remaining operative life of the emitting means and a display unit for indicating the life of said light emitting means.

13. The oximeter device according to claim 11, wherein sum check data is stored in said memory means for judging whether or not the contents of the memory means have been destroyed and whether or not the probe is operatively connected to the main unit.

14. The oximeter device according to claim 12 further including means for counting the emitting time of said light emitting means and estimating the light emitting intensity corresponding to the time of turning on said light emitting means and adjusting a driving current for said light emitting means based on the intensity and the emitting time.

15. In an improved oximeter device having a monitor with a processor circuit for calculating the saturation degree of oxygen, the improvement comprising:

a probe for connection to the monitor having a first light emitting means for emitting a predetermined first wavelength of light and a second light emitting means for emitting a predetermined second wavelength of light, a light receiving means for receiving the emitted light and converting it into electrical signals for subsequent processing by the processor circuit, and memory means for storing predetermined data characteristics of the probe to enable a calibrated processing of the electrical signals by the processor circuit, including the storage of data representative of the crosstalk noise of light received by the light receiving means containing a mix of first and second wavelengths of light, whereby the processor circuit can correct the processing of the electrical signals to remove the crosstalk noise.

16. The improved oximeter of claim 15 wherein the first and second light emitting means includes light emitting diodes.

17. An oximeter device for measuring the saturation degree of oxygen in arterial blood, comprising:

a probe having light emitting means for emitting light to an organism to be measured, light receiving means for receiving light from the organism, and memory means for storing predetermined data indicative of the amount of crosstalk received by said light receiving means;

a main unit having a calculation means which reads out the data stored in said memory means and calculates the saturation degree of oxygen in the basis of the read out data and the output of said light receiving means, and means for detachably connecting said probe to said main unit.

18. An oximeter device for measuring the saturation degree of oxygen in arterial blood, comprising:

a probe having light emitting means for emitting light to an organism to be measured, light receiving means for receiving light from the organism, and memory means for storing data indicative of the total time that said light emitting means is activated to emit light;

a main unit having a calculation means which calculates the saturation degree of oxygen on the basis of a read out of the output of said light receiving means and a control means for reading out the data stored in said memory means and for estimating the intensity of light to be emitted by said light emitting means on the basis of the read out data and to adjust the driving current of said light emitting means on the basis of said estimated intensity, and means for detachably connecting said probe to said main unit.

19. The oximeter device according to claim 18, further comprising a display unit for indicating the remaining operative life of said light emitting means.

20. An oximeter device for measuring the saturation degree of oxygen in arterial blood, comprising:

a probe having light emitting means for emitting light to an organism to be measured, light receiving means for receiving light from the organism, and first memory means for storing data necessary for measurement of a saturation degree of oxygen in arterial blood of an examined organism caused by said light emitting means and said light receiving means, and a main unit detachably connecting said probe, having second memory means for storing the data which is read out from said first memory means when electrical power is supplied to the oximeter device, a judging means which reads out the data stored in said first memory means repeatedly at a predetermined time period and compares said read out data with the data stored in said second memory means to judge whether or not the probe is exactly connected to the main unit, and a calculation means which calculates the saturation degree of oxygen on the basis of said read out data and the output of said light receiving means when said judging means judges said probe is exactly connected to said main unit.

21. An oximeter device for measuring the saturation degree of oxygen in arterial blood, comprising:

a probe having light emitting means for emitting light to an organism to be measured, light receiving means for receiving light from the organism, and memory means for storing a plurality of first data necessary for measurement of a saturation degree of oxygen in arterial blood of an examined organism caused by said light emitting means and said light receiving means and a second data indicative of a sum of said first data, and a main unit, detachably connecting said probe, having a judging means which reads out the data stored in said memory means and compares the read out second data with an added sum of the read out first data to judge whether or not the contents of the memory means are destroyed, and a calculation means which calculates the saturation degree of oxygen on the basis of said read out first data and the output of said light receiving means when said judging means judges that the contents of the memory means have not been destroyed.

22. An oximeter device for measuring the saturation degree of oxygen in arterial blood, comprising:

a probe having light emitting means for emitting light to an organism to be measured, light receiving means for receiving light from the organism, and memory means for storing data indicative of the intensity of light to be emitted by said light emitting means, a main unit having a reading means for reading out the data stored in said memory means, a control means for adjusting the driving current of said light emitting means on the basis of the read out of the data, and a calculation means for calculating the saturation degree of oxygen on the basis of the output of said light receiving means, and means for connecting said probe to said main unit.

23. An oximeter device for measuring the saturation degree of oxygen in arterial blood, comprising:

a probe having light emitting means for emitting a light of a first wavelength necessary for measurement of the saturation degree of oxygen to an organism to be measured, light receiving means for receiving light from the organism, and memory means for storing data indicative of the first wavelength and the half power width of light of a first wavelength;

a main unit having a calculation means which reads out the data stored in said memory means and calculates the saturation degree of oxygen on the basis of the read out data and the output of said light receiving means, and means for connecting said probe to said main unit.

24. The oximeter device according to claim 23, wherein said light emitting means further emits light of a second wavelength that is unnecessary for the measurement of the saturation degree of oxygen, and said memory means further stores data indicative of the second wavelength.

25. An oximeter device for measuring the saturation degree of oxygen in arterial blood, comprising:

a probe having light emitting means for emitting a first wavelength of light necessary for measurement of the saturation degree of oxygen and a second wavelength of light that is unnecessary for the measurement of the saturation degree of oxygen in an organism to be measured, light receiving means for receiving light from the organism, and memory means for storing data of the ratio of the intensity of light of the first wavelength to be emitted by said light emitting means to the intensity of light of the second wavelength to be emitted thereby;

a main unit having a calculation means which reads out the data stored in said memory means and calculates the saturation degree of oxygen on the basis of the read out data, including the ratio of intensity of the first and second wavelengths and the output of said light receiving means, and means for connecting said probe to said main unit.

26. An oximeter device for measuring the saturation degree of oxygen in arterial blood, comprising:

a probe having light emitting means for emitting light to an organism to be measured, light receiving means for receiving light from the organism, and memory means for storing, as data, the coefficients used in an equation for calculation of the saturation degree of oxygen and corresponding to the particular characteristics of the light emitting means;

a main unit having a calculation means which reads out the coefficients stored in said memory means and calculates the saturation degree of oxygen on the basis of the read out data and the output of said light receiving means, and means for detachably connecting said probe to said main unit.

27. An oximeter device for measuring the saturation degree of oxygen in arterial blood, comprising:

a main unit having a first memory means for storing the coefficients used in an equation for calculation of the saturation degree of oxygen;

a probe having light emitting means for emitting light to an organism to be measured, light receiving means for receiving light from the organism, and a second memory means for storing the calibration amount of the coefficients stored in said first memory means and corresponds to characteristics of the light emitting means;

means for detachably connecting said probe to said main unit;

said main unit further comprising a calculation means which reads out the calibration amount stored in said second memory means in said probe and calculates the saturation degree of oxygen on the basis of the calibration amount, the output of said light receiving means and the coefficients stored in said first memory means.

28. An oximeter device for measuring the saturation degree of oxygen in arterial blood, comprising:
   a main unit having a first memory means for storing a calculation table of the reference saturation degree of oxygen;
   a probe having light emitting means for emitting light to an organism to be measured, light receiving means for receiving light from the organism, and a second memory means for storing the calculation amount of the calibration table stored in said first memory means and corresponding to characteristics of the light emitting means, and
   means for detachably connecting said probe to said unit,
   said main unit further comprising a calculation means which reads out the calibration amount stored in said second memory means in said probe and calculates the saturation degree of oxygen on the basis of the calibration amount, the output of said light receiving means and the coefficients stored in said first memory means.

* * * * *